United States Patent [19]

Singer

[11] 4,349,019

[45] Sep. 14, 1982

[54] SURGICAL LEGGINGS

[75] Inventor: Wayne J. Singer, Woodstock, Ga.

[73] Assignee: Kimberly-Clark Corporation, Neenah, Wis.

[21] Appl. No.: 283,199

[22] Filed: Jul. 14, 1981

[51] Int. Cl.³ .............................................. A61F 13/00
[52] U.S. Cl. ............................................... 128/132 D
[58] Field of Search ............... 128/132 R, 132 D, 155, 128/156, 157

[56] References Cited

U.S. PATENT DOCUMENTS

| | | | |
|---|---|---|---|
| 3,335,719 | 8/1967 | Boucher | 128/132 D |
| 3,589,365 | 6/1971 | Sejman | 128/132 D |
| 3,613,676 | 10/1971 | Endres et al. | 128/132 D |
| 3,625,205 | 12/1971 | Madden et al. | 128/132 D |
| 3,707,964 | 1/1973 | Patience et al. | 128/132 D |
| 3,742,944 | 7/1973 | Sease | 128/132 D |
| 3,747,655 | 7/1973 | Hadtke | 128/132 D |
| 3,750,663 | 8/1973 | Collins | 128/132 D |
| 3,934,582 | 1/1976 | Gorrie | 128/132 D |
| 3,989,040 | 11/1976 | Lofgren et al. | 128/132 D |
| 4,308,864 | 1/1982 | Small et al. | 128/132 D |

FOREIGN PATENT DOCUMENTS 2460187 10/1975 Fed. Rep. of Germany ... 128/132 D

Primary Examiner—Kyle L. Howell
Assistant Examiner—T. J. Wallen
Attorney, Agent, or Firm—Leydig, Voit, Osann, Mayer and Holt

[57] ABSTRACT

A surgical cover or drape in the form of a loose fitting legging is disclosed which provides sterile coverage for the abdominal region as well as the legs while limiting undesirable excess material in the perineal area. The surgical cover or drape comprises a generally rectangular main body portion having first and second panels. These panels are secured to each other along their longitudinal edges and at one end to form a sleeve with an open end and a closed end. A cuff is secured to the first panel near the open end of the sleeve to assist the surgical team member fitting the legging over the patient's leg. The surgical cover or drape further comprises an abdominal cover flap secured along one edge to the second panel near the open end of the sleeve. The abdominal cover flap preferably has two generally parallel opposing edges of unequal length adjacent the edge secured to the panel and is so constructed and arranged as to provide substantial coverage for the abdominal area of the patient but with reduced material at the side of the patient and in the perineal area. Means are provided on the abdominal cover flap for securing it to the patient's abdomen or to the corresponding flap of the other legging.

7 Claims, 5 Drawing Figures

SURGICAL LEGGINGS

BACKGROUND OF THE INVENTION

1. Field of the Invention

The present invention relates generally to surgical and obstetrical cover means and, more particularly, to leggings especially adapted for use in obstetrical procedures and other surgical procedures carried out in the lithotomy position.

Surgical leggings have long been employed to cover body limbs during surgical procedures. Some drapes have leggings incorporated into a drape covering the major portion of a patient's body, i.e., the leggings are an integral part of the surgical drape. In certain procedures, particularly in obstetrics, complete coverage, as provided for with these surgical drapes in which the leggings are integral to a main body portion, is neither necessary nor desirable. It is, however, desirable in certain instances to provide sterile coverage for both the abdomen and the patient's legs. The subject invention is directed to such a legging, providing sterile coverage of the patient's legs as well as the abdomen, while avoiding excess material in the perineal area.

2. Summary of the Invention

This invention is directed to a surgical cover or drape in the form of a loose fitting legging which provides sterile coverage for a patient's leg while also providing sterile coverage for the patient's abdomen. When used in combination with a second legging, the abdominal cover flap, which is an integral part of the legging, provides substantially complete sterile coverage for the abdominal area of the patient.

The loose fitting legging of the subject invention comprises a generally rectangular main body portion having a first and second panel of like size, with the panels being longer than they are wide and secured to each other along their longitudinal edges and at one end, thereby forming a sleeve with an open end and a closed end. A flap is secured to one of the panels near the open end of the sleeve. It overlies the panel adjacent the open end of the sleeve and opens away from the open end of the sleeve. An abdominal cover forming an integral part of the legging is secured along one edge to the other panel, also at the open end of the sleeve. The abdominal cover, which comprises a flap having two generally parallel opposing edges of unequal length adjacent the edge secured to the second panel and generally parallel to the longitudinal edges of the main body of the legging, is so constructed and arranged as to provide substantial coverage for the abdominal area of the patient but with reduced material at the side of the patient and in the perineal area. The legging also has means for securing the abdominal cover flap to the patient's abdomen or to the corresponding abdominal cover flap of a second legging.

DESCRIPTION OF THE PREFERRED EMBODIMENTS

While the invention will be described in connection with a preferred embodiment, it will be understood that it is not intended to limit the invention to that embodiment. On the contrary, it is intended to cover all alternatives, modifications and equivalents as may be included within the spirit and scope of the invention.

Figure 1:
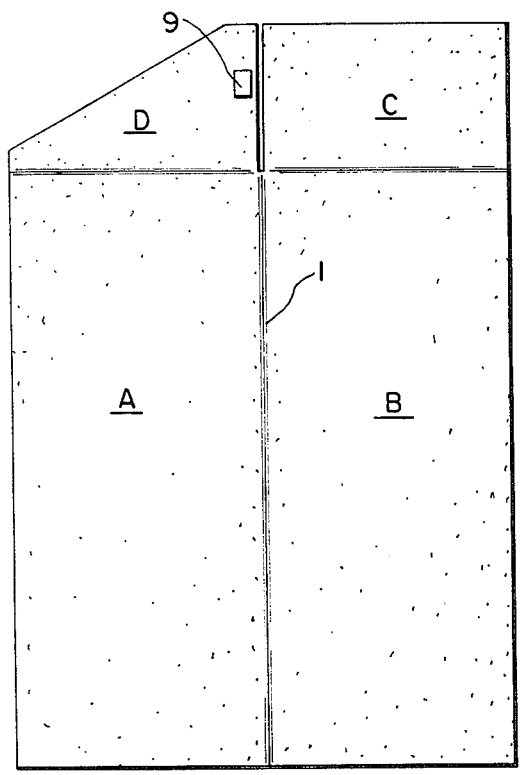
FIG. 1 is a plan view of a single piece of material from which the subject legging is manufactured in a preferred embodiment of the invention.
Figure 2:
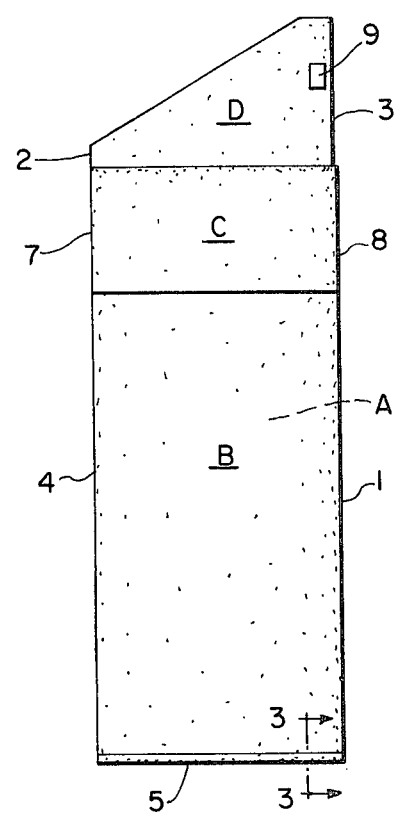
FIG. 2 is a plan view of a subsequent step in the manufacture of the legging wherein panel B has been folded over panel A and cuff C has been secured to panel B.
Figure 4:
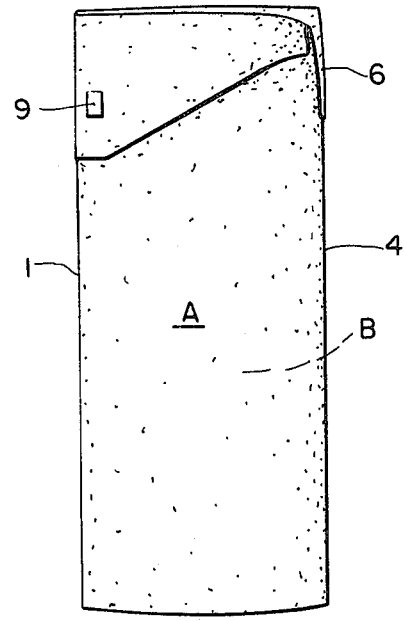
FIG. 4 is a back plan and slight perspective view of the completely formed legging with abdominal flap D folded down on panel A.

Turning now to the drawings and referring first to FIG. 1, a preferred method of making the legging of the subject invention is to start with a single piece of material, as depicted in FIG. 1. Specifically, the starting configuration for preparing the legging of the subject invention includes the preparation of a flat piece of material containing the parts disclosed in FIG. 1, specifically, a generally rectangular panel A longer than it is wide adjacent a second panel B of like size and shape. It should be noted that panels A and B in the preferred embodiment disclosed in FIG. 1 are connected along line 1, which in the finished legging is a longitudinal edge of the main body portion of the legging, as shown in FIGS. 2 and 4. Flap C, depicted in FIG. 1, when subsequently folded down, as depicted in FIG. 2, will form the cuff of the legging used for positioning the legging on the patient's leg. Pentagonal flap D, having substantially parallel sides 2 and 3 (but of unequal length), which are also substantially parallel to the longitudinal edges 1 and 4 of the main body portion made up of panels A and B, is the abdominal cover flap. It can be folded down onto panel A, as depicted in FIG. 4.

After material has been produced having the general shape depicted in FIG. 1, the manufacture of the legging proceeds as depicted in FIG. 2. Specifically, panels A and B are folded over so that, as shown in FIG. 2, panel B lies on top of panel A. Because they are of like size, panel A is substantially completely covered by panel B, as shown in FIG. 2. Panel A is then secured to panel B along the bottom edge 5 and along substantially the entire length of longitudinal edge 4. Edge 4 is desirably left open near the open end of the legging, as depicted in FIG. 4 at 6, to provide a larger opening to facilitate placing of the legging over the patient's leg and the stirrup holding the patient's leg and foot in position.

Figure 3:
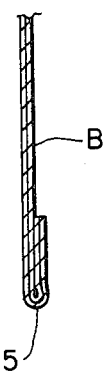
FIG. 3 is a cross section along line 3—3 of FIG. 2 showing the construction of the closed end of the legging.

The edge 5 is preferably strengthened by folding over the bottom portion of the panels, A and B, which have previously been secured to each other, and securing the folded over portion to either of panels A and B (see the cross section of the fold as shown in FIG. 3).

Flap C is folded down over panel B as shown in FIG. 2. It is then secured to panel B along edges 7 and 8 to form the cuff.

Abdominal cover flap D is preferably folded down, covering a portion of panel A as depicted in FIG. 4, prior to folding of the legging for packaging and shipment.

Abdominal cover flap D has attached thereto a securing means 9 for subsequently securing the cover to the patient's abdomen or, alternatively, to the corresponding flap on the second legging worn by the patient. Typically, securing means 9 is a suitable adhesive applied to the abdominal cover during the manufacture of the legging. Preferably, the adhesive will have a protective cover which is removed prior to attachment to the patient.

Figure 5:
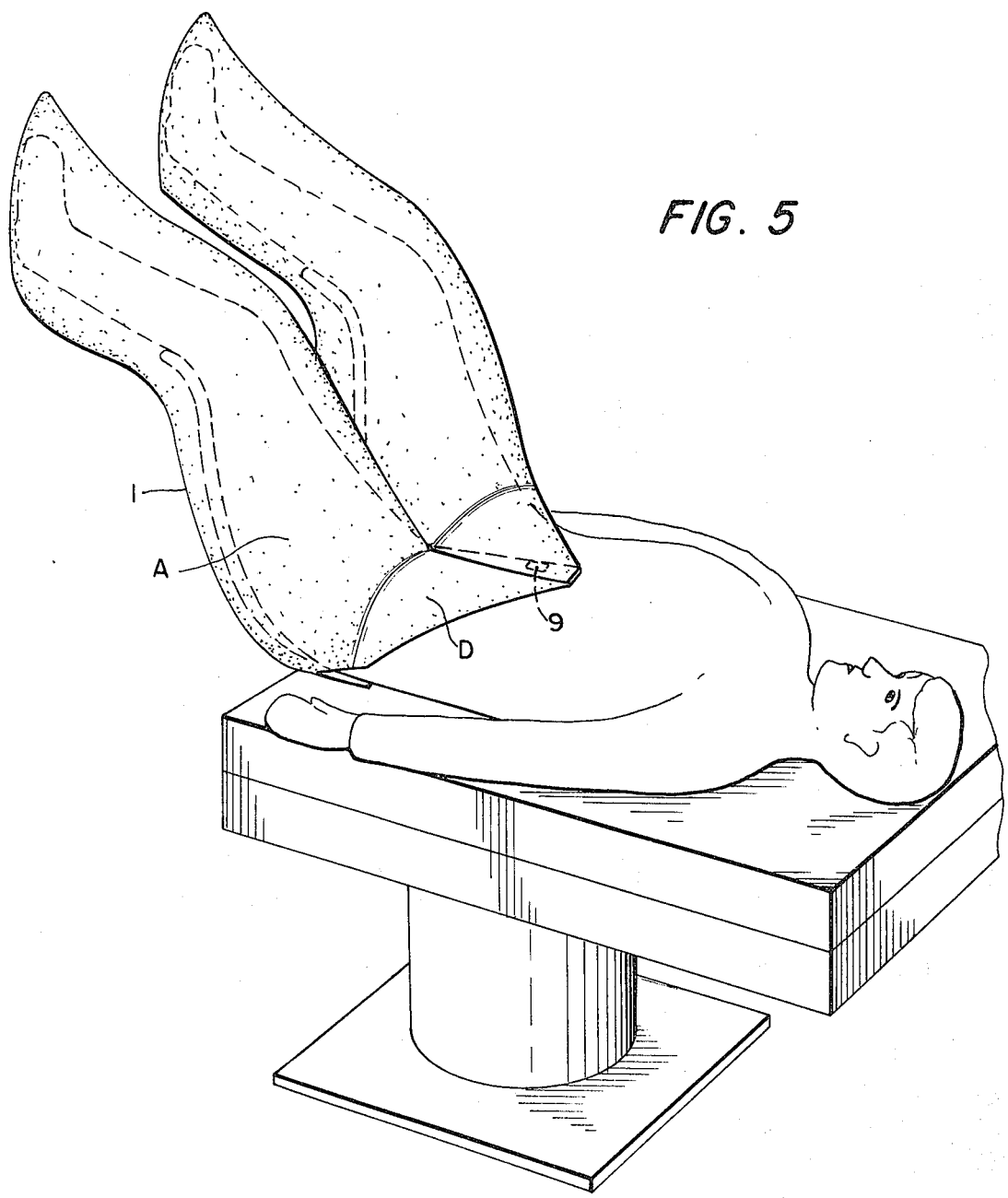
FIG. 5 is a perspective view of a patient wearing leggings of the subject invention and showing the coverage of the abdominal area by the subject invention.

The legging of the subject invention is placed on the patient's leg by a sterile member of the surgical team, who places his hand in the cuff of the legging and slides it over the patient's leg. (The legging depicted in FIGS. 1-4 is for the left leg. To form the right legging, flap D can be reversed with cuff C in FIG. 1.) After the legging is fitted over the patient's left leg, the abdominal cover is unfolded and placed over the abdomen, and securing means 9 is used to secure the abdominal cover D to the patient's lower abdomen. Identical steps are followed with the patient's right leg, except that the securing means on the right legging is preferably secured to the previously positioned left abdominal cover by overlapping the abdominal cover of the right legging over the abdominal cover of the left legging. FIG. 5 depicts the leggings in place on a patient. The overlap of the two abdominal covers provides complete coverage of the abdominal area as depicted in FIG. 5. Obviously, if the right legging is positioned first, the abdominal cover of the left legging will overlap that of the right legging.

It should be noted that modifications can be made in the manufacturing procedure for the legging of the subject invention. Specifically, a preferred embodiment of the subject invention calls for flap B to be separately cut and attached to panel A by appropriate means, e.g., adhesive, tape, or sewing. Similarly, although not a preferred embodiment, panels A and B can be prepared from individual pieces of material. This, of course, will entail the securing of the edges of panels A and B along both longitudinal edges and the bottom to produce a sleeve having an open and a closed end. Flap D need not be pentagonal in shape, as depicted in the preferred embodiment in the drawings. It can, for example, be triangular in shape, the primary requirement being that the side of the flap toward the center of the abdomen is longer than the outer edge to provide coverage for the abdomen while reducing the amount of material in the perineal area and along the side of the patient.

The subject invention is particularly useful with disposable or limited use leggings, albeit it is also useful with reusable leggings or drapes. Materials useful for making leggings of the subject invention include, by way of example, cotton, reinforced non-woven fabrics or any woven or non-woven fabric recognized in the art as appropriate for the manufacture of surgical drapes and the like. To secure the various pieces of legging to each other, conventional techniques can be used. For instance, adhesives, tape or sewing techniques can be used. When an adhesive is used, it can be a hot melt or latex adhesive.

As can be seen from the foregoing detailed description, the present invention provides an improved method of manufacturing a surgical cover or drape in the form of a legging providing sterile coverage of the abdominal area of a patient while reducing the amount of material on the sides and perineal area.

I claim:

1. A surgical cover or drape in the form of a loose fitting legging comprising
   (a) a generally rectangular main body portion having first and second panels of like size, said panels being longer than they are wide and secured to each other along their longitudinal edges and at one end, forming a sleeve with an open end and a closed end;
   (b) a cuff comprising a flap secured to said first panel near said open end of said sleeve and overlying said first panel adjacent to and opening away from said open end of said sleeve;
   (c) an abdominal cover comprising a flap secured along one edge to said second panel at said open end of said sleeve, said flap having two opposing edges of unequal length adjacent the edge secured to said second panel, said opposing edges generally parallel to each other and to the longitudinal edges of said main body portion, said flap so constructed and arranged as to provide substantial coverage for the abdominal area of a patient with reduced material at the side of the patient and in the perineal area; and
   (d) means for securing said abdominal cover to a patient's abdomen or to the corresponding abdominal cover of a second legging.

2. The surgical cover or drape of claim 1 wherein said cover or drape is disposable.

3. The surgical cover or drape of claim 1 wherein said means for securing said abdominal cover to a patient's abdomen is an adhesive.

4. The surgical cover or drape of claim 1 wherein said cover or drape is a single piece of material.

5. The surgical cover or drape of claim 1 wherein said abdominal cover is a separate piece of material secured to said second panel by an adhesive.

6. The surgical cover or drape of claim 1 wherein said abdominal cover is pentagonal in shape.

7. A surgical cover or drape in the form of a loose fitting legging comprising
   (a) a generally rectangular main body portion having first and second panels of like size, said panels being longer than they are wide and secured to each other along their longitudinal edges and at one end, forming a sleeve with an open end and a closed end;
   (b) a cuff comprising a flap secured to said first panel near said open end of said sleeve and overlying said first panel adjacent to and opening away from said open end of said sleeve;
   (c) an abdominal cover comprising a triangular flap secured along one edge of said second panel at said open end of said sleeve, said flap so constructed and arranged as to provide substantial coverage for the abdominal area of a patient with reduced material at the side of the patient and in the perineal area; and
   (d) means for securing said abdominal cover to a patient's abdomen or to the corresponding abdominal cover of a second legging.

* * * * *